(12) United States Patent
Castellini

(10) Patent No.: US 7,011,519 B2
(45) Date of Patent: Mar. 14, 2006

(54) DENTAL UNIT

(75) Inventor: Franco Castellini, Bologna (IT)

(73) Assignee: Casteleini S.p.A., Bologna (IT)

( * ) Notice: Subject to any disclaimer, the term of this patent is extended or adjusted under 35 U.S.C. 154(b) by 121 days.

(21) Appl. No.: 10/264,644

(22) Filed: Oct. 4, 2002

(65) Prior Publication Data
US 2003/0068596 A1 Apr. 10, 2003

(30) Foreign Application Priority Data
Oct. 10, 2001 (IT) .......................... BO2001A0623

(51) Int. Cl.
*A61G 15/14* (2006.01)
(52) U.S. Cl. ........................... 433/79; 433/49; 433/108
(58) Field of Classification Search ................. 433/49, 433/77, 78, 79, 98, 108; 312/209; 324/207.21, 324/207.24
See application file for complete search history.

(56) References Cited

U.S. PATENT DOCUMENTS

| | | | |
|---|---|---|---|
| 4,052,649 A | * | 10/1977 | Greenwell et al. .......... 318/765 |
| 4,760,317 A | | 7/1988 | Hetzel et al. |
| 4,857,842 A | * | 8/1989 | Sturman et al. ............ 324/225 |
| 4,934,933 A | * | 6/1990 | Fuchs .......................... 433/79 |
| 5,710,474 A | | 1/1998 | Mulgrave |
| 5,947,729 A | * | 9/1999 | Bell ............................. 433/98 |
| 6,149,430 A | * | 11/2000 | Nemetz et al. ............. 433/132 |
| 6,436,072 B1 | * | 8/2002 | Kullas et al. ............... 604/151 |

FOREIGN PATENT DOCUMENTS

| | | |
|---|---|---|
| DE | 197 14 248 A1 | 10/1998 |
| EP | 0 734 689 A1 | 10/1996 |
| EP | 1 228 737 A2 | 8/2002 |

OTHER PUBLICATIONS

European Search Reporting corresponding to European Application No. EP 02 42 5590.

* cited by examiner

*Primary Examiner*—Cary E. O'Connor
*Assistant Examiner*—Candice C. Stokes
(74) *Attorney, Agent, or Firm*—Fay, Sharpe, Fagan, Minnich & McKee, LLP

(57) ABSTRACT

A dental unit comprises at least one chair, a base, positioned next to the chair and mounting a handpiece tray. The tray is equipped with a plurality of operative or auxiliary handpieces for dental operations of traditional conservative type and/or for implants. At least one of the handpieces is fitted with a drive unit consisting of a brushless micromotor presenting a unit for continuously controlling the speed of the brushless micromotor according to parameters that depend on the type of application, that is, traditional, conservative type operations or implants.

4 Claims, 2 Drawing Sheets

DENTAL UNIT

BACKGROUND OF THE INVENTION

The present invention relates to a dental unit.

At present, a dental unit in its most basic form typically consists of a chair and a base or column which mounts the main and auxiliary items of dental equipment, including a tray for a main set of handpieces and another tray for an accessory set of handpieces.

The dental unit is normally equipped with a plurality of dental handpieces, divided substantially into instruments, for example, the turbine and the micromotor, used for removal of dental material, and instruments, for example, the syringe and the polymerizing lamp, used for complementary stages of dental treatment.

These handpieces may be located, according to function, either on the main tray or on the accessory tray.

With the passage of time, this basic structure has been constantly improved in both the internal and external features of the dental unit. Thus, the latest dental units include sophisticated water and compressed air systems, one or more microprocessor units designed to control the functions of the dental unit, and other technological developments.

These developments have also greatly improved the operative parts of dental units, for example, the handpieces, and especially micromotors, which the present invention is concerned with in particular. A handpiece typically comprises a first body, constituting the part by which the handpiece is held and which is equipped on the end of it with a head to which a tool (for example, a burr) can be fitted.

In micromotor handpieces, the first body is connected to a second body, which houses a motor. The connection is coaxial by means of a quick-release fitting on the respective ends of the two bodies. The second body is in turn connected, at its other end, to an endpiece that supplies water or physiological saline, air for nebulizing the liquid, air for cooling the micromotor and electricity for driving the micromotor. The endpiece constitutes the end of a cable that starts at one of the aforementioned handpiece trays on a dental unit and that combines the conduits and wires used to supply the fluids and electricity required for the operation of the handpiece.

The performance of these handpieces, driven by conventional electric motors, has reached the highest possible levels, giving little room for further improvement. The Applicant has therefore designed a handpiece which, instead of a conventional electric motor with brushes, is driven by a brushless motor. This optimizes speed control, offers better torque response and silent operation, and reduces friction and heating, thereby increasing the useful life of the motor. In addition to this, the new handpiece can be used for both traditional, conservative treatments and for implants thanks to a constructional architecture that enables it to be fitted with all the tools and accessories currently used on traditional handpieces.

SUMMARY OF THE INVENTION

The present invention accordingly provides a dental unit comprising at least one chair, a base positioned next to the chair and mounting a handpiece tray. The tray is equipped with a plurality of operative or auxiliary handpieces for dental operations of traditional conservative type and/or for implants. At least one of the handpieces is fitted with a drive unit consisting of a brushless micromotor presenting a unit for continuously controlling the speed of the brushless micromotor according to parameters that depend on the type of application, that is, traditional conservative type operations or implants.

BRIEF DESCRIPTION OF THE DRAWINGS

The technical characteristics of the invention, with reference to the above aims, are clearly described in the claims below and its advantages are apparent from the detailed description which follows, with reference to the accompanying drawings which illustrate a preferred embodiment of the invention provided merely by way of example without restricting the scope of the inventive concept, and in which:

DESCRIPTION OF THE PREFERRED EMBODIMENTS

Figure 1:
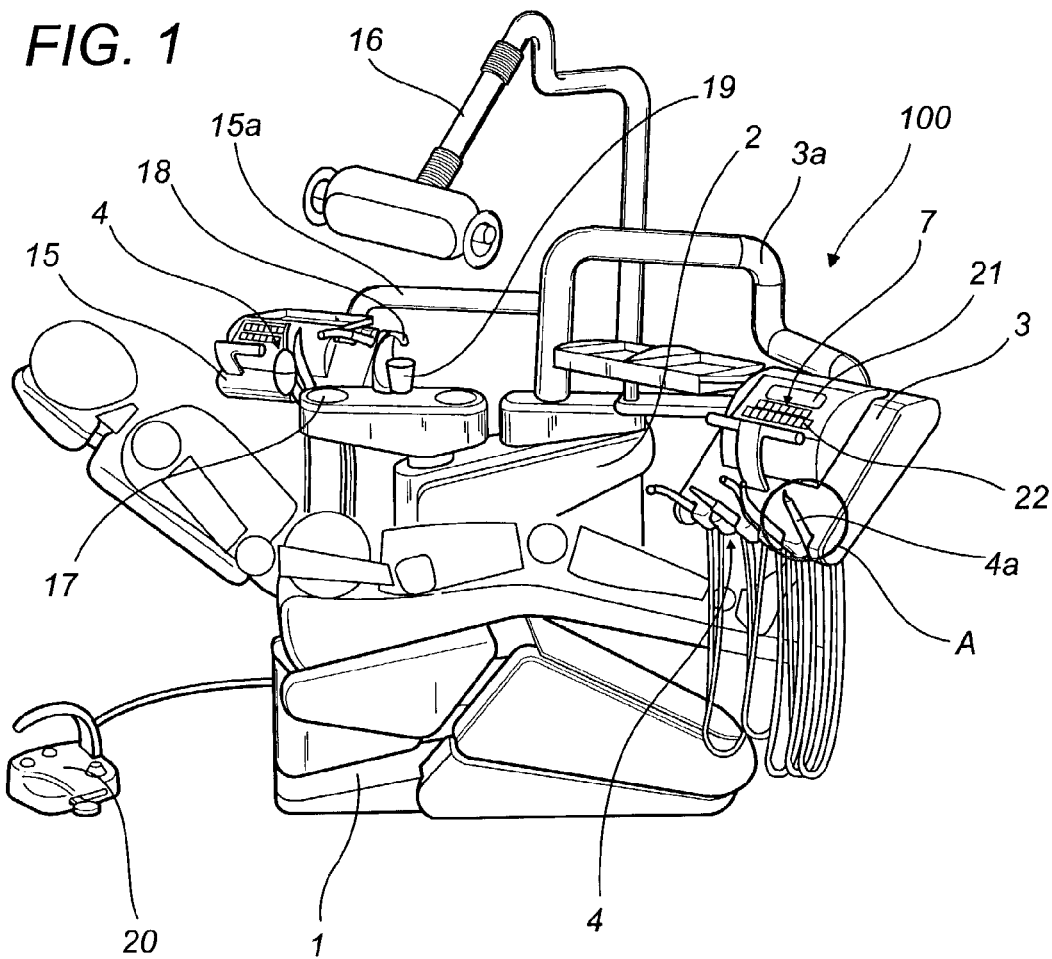
FIG. 1 shows a dental unit according to the present invention in a schematic perspective view with some parts cut away to better illustrate others.

With reference to the accompanying drawings, in particular FIG. 1, the dental unit according to the present invention, labeled 100 in its entirety, essentially comprises a chair 1, a base or column 2, located next to the chair 1 and mounting a set of operative and auxiliary elements such as a main handpiece tray 3 on an arm 3a.

FIG. 1 also shows a second tray 15 for the dentist's assistant, mounted on a second arm 15a, a lamp 16, a spit bowl 17, an endpiece 18 for supplying water to a tumbler 19, and a pedal unit 20 for activating the handpieces.

The handpieces 4 are mounted on the two trays 3 and 15 and are divided into operative and auxiliary handpieces for traditional, conservative operations and/or for implants.

The dental unit 100 further comprises a microprocessor unit 7 for controlling the main and auxiliary functions of the dental unit 100, that is, the main operative functions of the handpieces, such as, for example, speed, rpm, air and water supply, including the main water supply for the dental unit, activation of disinfection/sterilization cycles, etc.

The unit 7 may be equipped with a display unit 21 and a keyboard 22, both located, for example, on the tray 3.

In a dental unit 100 structured in this way, at least one of the handpieces, for example the one labeled 4a in FIG. 1, is fitted with a drive unit 5 consisting of a brushless micromotor (see also FIG. 2) presenting a unit 6 for continuously controlling the speed of the brushless micromotor 5 according to parameters that depend on the type of application, that is, traditional, conservative type operations or implants.

Preferably, the unit 6 for continuously controlling the speed of the handpiece 4a is controlled by the microprocessor unit 7 with which it is possible to set the user parameters according to the type of application.

Figure 2:
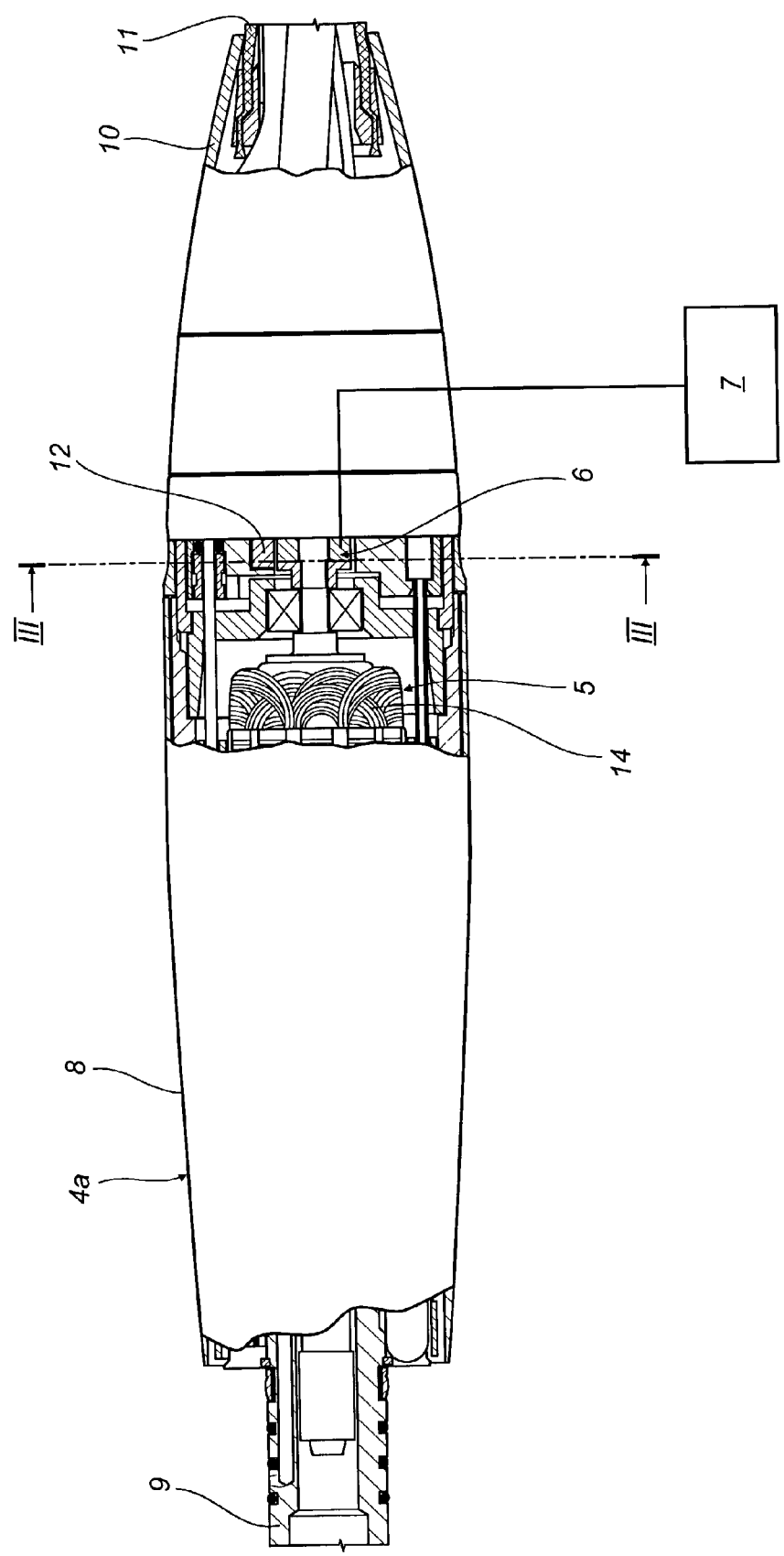
FIG. 2 is a schematic side view of a detail A from FIG. 1 showing a handpiece fitted to the dental unit.

As shown in FIG. 2, the handpiece 4a comprises an operative body 8, a spindle 9 located at a first end of the operative body 8 for quick fitting to the tool holder endpiece (not illustrated).

The tool drive unit 5 is housed in the operative body 8, while the other end of the operative body 8 mounts an endpiece 10 presenting at least one power cable 11 for the drive unit 5, the cable 11 being connected to the customary circuitry of the dental unit 100.

The unit 6 for continuously controlling the speed of the handpiece 4a is housed in the operative body 8 and comprises a plurality of Hall-effect sensors 12.

Figure 3:
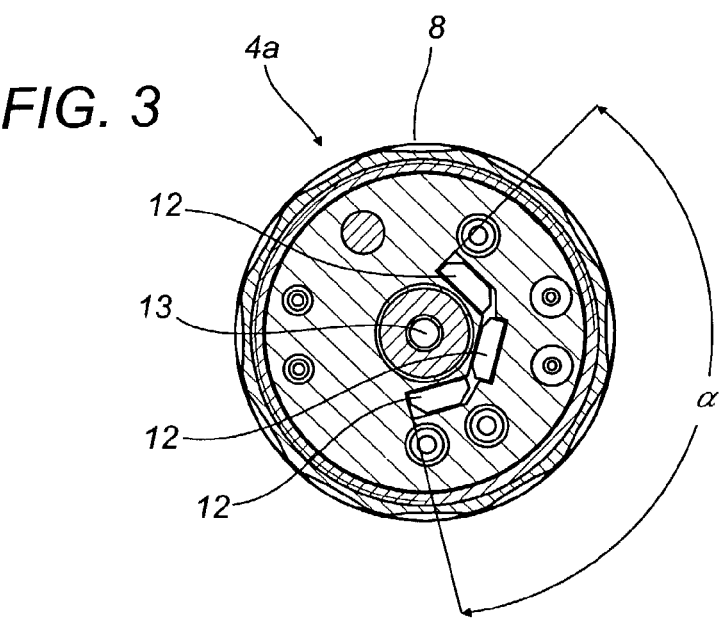
FIG. 3 is a cross section through line III—III of FIG. 2.

Looking in more detail (see FIG. 3), the unit 6 for continuously controlling the speed of the handpiece 4a comprises three Hall-effect sensors 12.

These three Hall-effect sensors 12 are arranged at a defined angular interval α of approximately 120° around a reference magnet 13 associated to a rotor 14 of the brushless micromotor 5 in such a way as to detect the latter's position and provide feedback control of the speed of the rotor 14.

Obviously, the handpiece 4a is structured in such a way as to include all the conduits necessary to supply air and spray water for the tool and to illuminate the tool working area (these structures being of customary type and therefore not illustrated in detail).

A further improvement to the dental unit structured in this way adds to the unit's already wide range of operative capabilities.

Thus, the possibility of combining traditional handpieces with one or more brushless micromotor handpieces built directly into the dental unit makes it possible to extend the range of operations that can be performed on the patient using normal equipment and the units forming part of the dental unit itself.

Indeed, the brushless handpiece, or handpieces, receives fluids and motive power from the dental unit and the operative part of the handpiece is controlled directly by the microprocessor unit that controls the dental unit.

That means that auxiliary equipment independent of the dental unit, for example, for implant operations, are no longer necessary.

The wide range of speeds offered by the brushless motor enables the handpiece to be used for many different traditional treatments without having to change the handpiece, while at the same time allowing the speed to be controlled with a high degree of precision.

The invention described can be subject to modifications and variations without thereby departing from the scope of the inventive concept. Moreover, all the details of the invention may be substituted by technically equivalent elements.

What is claimed is:

1. A dental unit of the type comprising at least one chair, a base, positioned next to the chair and mounting a handpiece tray, the tray being equipped with a plurality of operative or auxiliary handpieces for dental operations of traditional conservative type and/or for implants; wherein at least one of the handpieces is fitted with a drive unit comprising a brushless micromotor presenting a unit for continuously controlling the speed of the brushless micromotor according to parameters that depend on the type of application, that is, traditional, conservative type operations or implants; the dental unit being fitted with a microprocessor unit for controlling the main and auxiliary functions of the dental unit, wherein the unit for continuously controlling the speed of the handpiece is controlled by the microprocessor unit and comprises a plurality of Hall-effect sensors arranged around a reference magnet associated to a rotor of the brushless micromotor.

2. The dental unit according to claim 1, where the handpiece includes an operative body, a spindle located at a first end of the operative body for quick fitting to the handpiece that mounts a tool, a tool drive unit housed in the operative body, and an endpiece fitted with at least one cable for powering the drive unit, the power cable being located at the other end of the operative body and being connected to the circuitry of the dental unit, wherein the unit for continuously controlling the speed of the handpiece is housed in the operative body and comprises said Hall-effect sensors.

3. The dental unit according to claim 1, wherein the unit for continuously controlling the speed of the handpiece comprises three Hall-effect sensors.

4. A dental unit of the type comprising at least one chair, a base, positioned next to the chair and mounting a handpiece tray, the tray being equipped with a plurality of operative or auxiliary handpieces for dental operations of traditional conservative type and/or for implants; wherein at least one of the handpieces is fitted with a drive unit comprising a brushless micromotor presenting a unit for continuously controlling the speed of the brushless micromotor according to parameters that depend on the type of application, that is, traditional, conservative type operations or implants; the dental unit being fitted with a microprocessor unit for controlling the main and auxiliary functions of the dental unit, wherein the unit for continuously controlling the speed of the handpiece is controlled by the microprocessor unit and comprises three Hall-effect sensors arranged at a defined angular interval of approximately 120° around a reference magnet associated to a rotor of the brushless micromotor.

* * * * *